(12) United States Patent
Havey et al.

(10) Patent No.: US 7,308,314 B2
(45) Date of Patent: Dec. 11, 2007

(54) METHOD AND APPARATUS FOR SENSORY SUBSTITUTION, VISION PROSTHESIS, OR LOW-VISION ENHANCEMENT UTILIZING THERMAL SENSING

(75) Inventors: Gary David Havey, Maple Grove, MN (US); Paul Lorn Gibson, Andover, MN (US); Gregory John Seifert, St. Paul, MN (US); Scott Kalpin, Cambridge, MN (US)

(73) Assignee: Advanced Medical Electronics, Minneapolis, MN (US)

( * ) Notice: Subject to any disclaimer, the term of this patent is extended or adjusted under 35 U.S.C. 154(b) by 504 days.

(21) Appl. No.: 10/454,295

(22) Filed: Jun. 4, 2003

(65) Prior Publication Data

US 2004/0030383 A1    Feb. 12, 2004

Related U.S. Application Data

(60) Provisional application No. 60/386,036, filed on Jun. 6, 2002.

(51) Int. Cl.
*A61N 1/36* (2006.01)
(52) U.S. Cl. ........................................ 607/54
(58) Field of Classification Search ............ 607/2, 607/53, 54; 600/558; 434/114; 250/330, 250/332
See application file for complete search history.

(56) References Cited

U.S. PATENT DOCUMENTS 3,612,061 A    10/1971  Collins et al.
4,154,503 A *  5/1979  Lettington et al. .......... 385/142
4,698,701 A    10/1987  Gantzhorn, Jr. et al.

(Continued)

OTHER PUBLICATIONS

Recent advances in portable infrared imaging systems. Grenn, M.W. Engineering in Medicine and Biology Society, 1996. Bridging Disciplines for Biomedicine. Proceedings of the 18th Annual Intl. Conf. of the IEEE. vol. 5. Oct. 31-Nov. 3, 1996. pp. 2083-2084.*

(Continued)

*Primary Examiner*—Mark Bockelman
*Assistant Examiner*—Eric D. Bertram
(74) *Attorney, Agent, or Firm*—Leffert Jay & Polglaze, P.A.

(57) ABSTRACT

A sensory substitution device according to an embodiment of the invention includes a thermal imaging array for sensing thermal characteristics of an external scene. The device includes a visual prosthesis adapted to receive input based on the scene sensed by the thermal imaging array and to convey information based on the scene to a user of the sensing device. The visual prosthesis is adapted to simultaneously convey to the user different visual information corresponding to portions of the scene having different thermal characteristics. One type of thermal imaging array includes a microbolometer imaging array, and one type of visual prosthesis includes a retinal implant. According to additional embodiments, an apparatus for obtaining thermal data includes a thermal detector adapted to sense thermal characteristics of an environment using a plurality of pixels. The apparatus also includes a pixel translator, operably coupled with the thermal detector, adapted to translate pixel data of the thermal detector to a lower resolution. The apparatus also includes an interface, operably coupled with the pixel translator, adapted to communicate the thermal characteristics of the environment to a user of the apparatus at a lower resolution than sensed by the thermal detector.

20 Claims, 13 Drawing Sheets

U.S. PATENT DOCUMENTS

| | | | |
|---|---|---|---|
| 4,712,003 A | | 12/1987 | Ban et al. |
| 5,065,024 A | * | 11/1991 | McCullough ............... 250/334 |
| 5,465,080 A | | 11/1995 | Liddiard et al. |
| 5,487,669 A | | 1/1996 | Kelk |
| 5,532,484 A | * | 7/1996 | Sweetser et al. ............ 250/332 |
| 5,554,849 A | | 9/1996 | Gates |
| 5,734,427 A | * | 3/1998 | Hayashi ................. 348/333.11 |
| 5,807,111 A | | 9/1998 | Schrader |
| 5,834,776 A | | 11/1998 | Beratan et al. |
| 5,838,238 A | | 11/1998 | Abita et al. |
| 5,895,233 A | | 4/1999 | Higashi et al. |
| 5,895,415 A | * | 4/1999 | Chow et al. .................. 607/54 |
| 5,912,660 A | | 6/1999 | Gouzman et al. |
| 5,933,082 A | | 8/1999 | Abita et al. |
| 5,935,155 A | * | 8/1999 | Humayun et al. ............ 607/54 |
| RE36,615 E | | 3/2000 | Wood |
| 6,044,632 A | * | 4/2000 | Schmalz et al. ......... 56/10.2 R |
| 6,055,048 A | * | 4/2000 | Langevin et al. ........ 356/237.1 |
| 6,114,697 A | | 9/2000 | Eden et al. |
| 6,195,168 B1 | * | 2/2001 | De Lega et al. ............ 356/497 |
| 6,204,961 B1 | * | 3/2001 | Anderson et al. ........... 359/353 |
| 6,278,441 B1 | | 8/2001 | Gouzman et al. |
| 6,298,010 B1 | | 10/2001 | Ritz et al. |
| 6,430,450 B1 | | 8/2002 | Bach-y-Rita et al. |
| 6,496,200 B1 | | 12/2002 | Snibbe et al. |
| 6,690,014 B1 | * | 2/2004 | Gooch et al. ............ 250/338.4 |
| 2002/0005778 A1 | * | 1/2002 | Breed et al.1 ............... 340/435 |
| 2002/0143257 A1 | | 10/2002 | Newman et al. |
| 2003/0128182 A1 | * | 7/2003 | Donath et al. .............. 345/156 |

OTHER PUBLICATIONS

Baker, Andrea, "Electronic 'Eye' Guides the Blind," Design News, Jun. 1993, pp. 87-89.*
"Poly IR: Fresnel Lenses for Infrared Wavelengths". Fresnel Technologies. 1997. www.fresneltech.com/pdf/POLYIR.pdf.*
Baker, Andrea, "Electronic 'Eye' Guides the Blind," *Design News*, Jun. 1993, pp. 87-89.
"Science & Technology—Virtual Reality, Navigating by Sound, " *Popular Science,* Oct. 1993, p. 32.
Stover, Dawn, "Science & Technology—Navigation, Leading the Blind," *Popular Science,* Dec. 1997, p. 17.
"Sight-to-Touch Translator," *NASA's Jet Propulsion Laboratory,* Pasadena, California, Mar. 1998.
Ram, Sunita, et al., "The People Sensor: A Mobility Aid for the Visually Impaired," *IEEE,* 1998, pp. 166-167.
Ertan, Sevgi, et al., "A Wearable Haptic Navigation Guidance System," *IEEE,* 1998, pp. 164-165.
Tadokoro, Y., et al., "Portable Traveling Navigation System for the Blind and its Application to Traveling Training System," *IEEE,* 1999, p. 589.
"Tounge Seen as Portal to the Brain," *News@ UW-Madison,* Feb. 2001.

* cited by examiner

METHOD AND APPARATUS FOR SENSORY SUBSTITUTION, VISION PROSTHESIS, OR LOW-VISION ENHANCEMENT UTILIZING THERMAL SENSING

CROSS-REFERENCE TO RELATED APPLICATION

The subject matter of this application is related to the subject matter of U.S. Provisional Patent Application No. 60/386,036, filed Jun. 6, 2002, which is incorporated herein by reference.

STATEMENT OF FEDERALLY SPONSORED RESEARCH AND DEVELOPMENT

This invention was made with government support under Cooperative Agreement No. DAMD17-97-2-7016 awarded by the U.S. Army Medical Research Acquisition Activity to the National Medical Technology Testbed, Inc. The government has certain rights in the invention.

BACKGROUND OF THE INVENTION

1. Field of the Invention

Embodiments of the present invention relate to electronic aids for the blind (or individuals with low vision) and prosthetic vision. Thermal imaging is disclosed as an alternative to or enhancement to visible imaging, resulting in an improved interpretation of an observed scene.

2. Description of Related Art

It is estimated that 120,000 Americans are totally blind and several million Americans experience significant vision loss. Devices developed to aid and assist blind and low-vision persons generally fall into the following categories: sensory substitution, sensory augmentation, visual prostheses, and low-vision enhancement devices. Sensory substitution and visual prosthetic devices are applicable to blind and low-vision persons. Sensory augmentation and low-vision enhancement devices are only applicable to persons that still have some amount, however limited, of operative vision.

Sensory substitution is a method that utilizes sensors to feed an annunciation device that stimulates an alternative sense. In a typical configuration, a camera is connected to a device that generates audio cues or a device that stimulates the sense of touch (i.e., haptic). Haptic devices can be electrostatic stimulation arrays, electromechanical pin arrays, or an array of electromechanical vibrators. Sensory augmentation methods operate similar to sensory substitution but assume that some amount of vision is still present in the person.

Visual prosthetic methods attempt to replace or bypass the specific inoperative biological functions with synthetic devices or implants in order to restore the overall visual function. One type of visual prosthetic method uses electronic sensors to direct the image of a retinal stimulating implant.

Low-vision enhancement devices use electronics and/or optics to magnify, enhance, or warp a visual scene in a manner that maximizes perception for persons who have lost aspects of their visual function.

Traditionally, a problem that devices based on each of these methods have in common has been the low effective bandwidth of the information channel. Audio, haptic, and even retinal stimulation implant devices can only provide a small portion (<1%) of the information bandwidth of a well-functioning eye.

Traditionally, each of these assistive methods have utilized visible light video cameras as the primary input sensor. There has been recent research and experimentation with the use of electrotactile arrays (also called haptic displays) to communicate visual images (normal light) to the blind. Fundamentally, it is a very complex problem to translate an image in a real world environment into meaningful tactile data. Image recognition techniques to identify edges of different separate objects must be used. This level of processing is not very practical in wearable applications. The use of thermal imaging has not been explored because in the past cryogenically cooled thermal cameras have been too expensive and too bulky to be practical.

Thermal Imaging

The electromagnetic spectrum includes ultraviolet (wavelengths from 0.1 to 0.4 micrometers), visible (from 0.4 to about 0.75 micrometers), near-infrared (from 0.75 to 1.2 micrometers), mid-infrared (from 2 to 5 micrometers) and far-infrared (from 8 to 14 micrometers). All materials at temperatures above zero degrees Kelvin emit infrared radiation. Most naturally occurring terrestrial objects have peak infrared emissions in the 8 to 14 micrometer range (far-infrared). Thermal imaging is done in the 8 to 14 micron range. In this range glass is opaque. Thermal imaging is done with lenses made of material such as germanium. Germanium is opaque to visible light. It is not presently considered possible for a visible light imager to share the same optics as a thermal imager.

Early thermal imaging systems developed in the 1970s and 1980s were unwieldy and did not lend themselves well to many applications. Physically large and technically complex, they required expensive liquid nitrogen or similar cryogenic cooling systems. Thermal imaging systems have been slow in delivering greater operational flexibility because of the cost, size, and weight of the cryogenic cooling components used in prior generations of high-performance IR sensors, and because of the size and power consumption of the supporting electronics.

In the early 1990s, a revolutionary suite of imaging radiation sensors was developed (see, e.g., U.S. Pat. Nos. RE036615, 6,114,697, 5,554,849, and 5,834,776, all of which are incorporated herein by reference). These sensors were revolutionary because they are mass-producible from materials such as low-cost silicon, and they operate well at room temperatures (hence termed "uncooled").

Uncooled IR sensors, such as of the microbolometer type, typically include arrays of microscopic bridge-like structures micromachined from silicon. Given the extremely low mass of the microbridge structures (typically on the order of a nanogram), they respond to very low radiation levels. Accurate measurements of microbridge temperature changes are used to quantify incident thermal radiation. Common methods for measuring microbridge temperatures include the use of thin-film thermocouples to generate a thermoelectric (TE) signal, or the use of thin-film resistors that undergo resistance changes according to temperature.

The basic operating principle of an uncooled silicon IR detector is as follows. Thermal energy in the 8 to 14 micron wavelength emitted from the target object is focused onto an extremely low mass microstructure. The incident energy is absorbed by the microstructure and causes an increase in the temperature of the bulk of the material. This temperature rise can be exactly correlated to the temperature at the optically corresponding point on the target.

Known uncooled IR imaging sensors include arrays of microscopic (typically 0.05 mm wide and 0.001 mm thick) bridge-like structures "micromachined" into silicon wafers by photolithographic processes similar to those used to make microprocessors. Calculation of the heating of microbolometers produced by focused IR radiation can be made using the well-known physical laws of radiation, and such microbolometers can measure temperature changes in a remote object with sensitivity well below 0.1° C.

For best sensitivity, microbolometer arrays should operate in an air pressure of 50 mTorr or less in the vicinity of the pixels, to eliminate thermal loss from the pixel to the air. To minimize size and weight and production costs, a process disclosed in U.S. Pat. No. 5,895,233, incorporated herein by reference, discloses a device allowing the completed array to have an infrared-transparent silicon top cap hermetically attached, to form an all-silicon integrated vacuum package (IVP). This technique allows a microbolometer imaging array to have small dimensions. Known microbolometer packages require a vacuum-sealed package around the outside of the microbolometer, resulting in larger diameters. Arrays are typically close-packed across the wafer, with a very small spacing to allow wafer sawing to separate completed arrays.

Because the sensors are fabricated using silicon photolithography, it is cost-effective to fabricate large one-dimensional (1D) and two-dimensional (2D) arrays complete with monolithic silicon readout electronics if required for a particular application. Two-dimensional arrays of IR sensors may be used with an IR-transmitting lens to produce a 2D temperature map of a target, analogous to the way a visible camera produces a two-dimensional image of a target.

Other methods have also been developed to construct arrays of infrared radiation detectors, including the use of pyroelectric detector elements, p-n junction devices, micro-cantilevers, or photoconductive or photovoltaic bandgap materials.

Blind and Low Vision

An application of infrared temperature measurement called the "People Sensor" is disclosed in Ram, S., et al., "The People Sensor: A Mobility Aid for the Visually Impaired", IEEE, 1998, pp. 166-167. The People Sensor combines an ultrasonic distance sensor with a pyroelectric IR sensor, to determine if an object that was identified by the ultrasonic sensor was animate (human) or inanimate (non-human). Only a single point measurement was taken.

There has been a history of work involving people attempting to use visible light images as an input to some type of haptic interface to a person. In the 1960s, Dr. James Bliss and his colleagues developed the Optacon, a tactile sensory substitution reading aid for the blind. The Optacon consists of a 6×24 element photodiode (light-sensitive) array that is mapped onto a 6×24 matrix of vibrating reeds, where the user places his finger to sense the image picked up by the light-sensing array. Subjects trained on this device were able to achieve reading rates of 60 words per minute.

Also in the 1960's, at the Smith-Kettlewell Institute of Visual Science, Dr. Bach-y-Rita and his colleagues developed a large electromechanical array of 400 points mounted in a chair which would transmit patterns of vibration onto the back of a person sitting in the chair. The patterns of vibration were dictated by the images sensed by a television camera under the control of the person in the chair. If the camera were directed towards a white vertical line on a black background for instance, the person would feel a vertical line on their back. If the camera were moved to the right, they would feel the line move correspondingly on their back. Although such a system did not have anywhere near the ability of the human eye to gather visual information, it showed that the brain was indeed capable of perceiving visual information through the skin.

Because electromechanical components are noisy, costly, consume a lot of electrical power, and have very limited reliability, efforts were made to develop electrical tactile stimulators. While these efforts were able to overcome many of the problems associated with electromechanical stimulators, new problems with comfort of sensation and skin irritability, and oftentimes even skin burns surfaced. These problems would have to be overcome before electrical stimulation could be practically used in tactile feedback applications. In the early 1990's ways to develop a multi-channel electrotactile system that would be able to stimulate the skin in a safe and comfortable manner began to be developed. This work was led by Kurt Kaczmarek at the University of Wisconsin. A recent example of a haptic interface of visible imaging is U.S. Pat. No. 6,055,048, which is incorporated herein by reference. In this patent, an optical sensor is described that operates in the far ultraviolet, visible and near infrared (up to 1 micron wavelength). A person who also has a haptic interface to sense patterns created from the processed optical sensor wears the sensor. The patent states that a microprocessor on the person has algorithms to recognize common shapes such as traffic lights, trees, cars, doorways and so forth. In an actual system this type of processing would be very difficult and require extremely high processing power.

There have been other applications of infrared light used as part of an aid or assist device for blind and low-vision persons. These applications typically use infrared for signaling or orientation. This is similar to applications of infrared for remote controls and uses near infrared wavelengths (0.75 to 1.2 microns). Near infrared has been used as an alarm system for blind and visually impaired persons (see U.S. Pat. Nos. 5,838,238 and 5,933,082, which are incorporated herein by reference). Installed devices create beams of near infrared light to warn a person when they are approaching a hazardous area. This is an example of near infrared being used to signal and provide orientation. Another example is given in a paper by Ertan et al. from MIT. In this example, ceiling-mounted infrared transceivers are used as a signal to a person to identify which room they are in.

Near infrared light has been used to provide distance information to a blind or low-vision person (see U.S. Pat. Nos. 5,487,669, 6,298,010, and 5,807,111, incorporated herein by reference). In these applications the blind person would use one or more IR distance measurement device to provide them warnings or orientation to obstacles and barriers. In these applications a laser or other IR light source is reflected from the obstacle or barrier and sensed by a device used by the blind or low vision person.

SUMMARY OF THE INVENTION

A sensory substitution device according to an embodiment of the invention includes a thermal imaging array for sensing thermal characteristics of an external scene. The device includes a visual prosthesis adapted to receive input based on the scene sensed by the thermal imaging array and to convey information based on the scene to a user of the sensing device. The visual prosthesis is adapted to simultaneously convey to the user different visual information corresponding to portions of the scene having different thermal characteristics. One type of thermal imaging array includes a microbolometer imaging array, and one type of visual prosthesis includes a retinal implant. According to additional embodiments, an apparatus for obtaining thermal data includes a thermal detector adapted to sense thermal characteristics of an environment using a plurality of pixels. The apparatus also includes a pixel translator, operably coupled with the thermal detector, adapted to translate pixel data of the thermal detector to a lower resolution. The apparatus also includes an interface, operably coupled with the pixel translator, adapted to communicate the thermal characteristics of the environment to a user of the apparatus at a lower resolution than sensed by the thermal detector.

Other aspects and features of the invention in its various embodiments will be apparent from the remainder of this patent application.

BRIEF DESCRIPTION OF THE DRAWINGS

Embodiments of the invention will be described with respect to the figures, in which like reference numerals denote like elements, and in which.

DETAILED DESCRIPTION OF PREFERRED EMBODIMENTS

Figure 1:
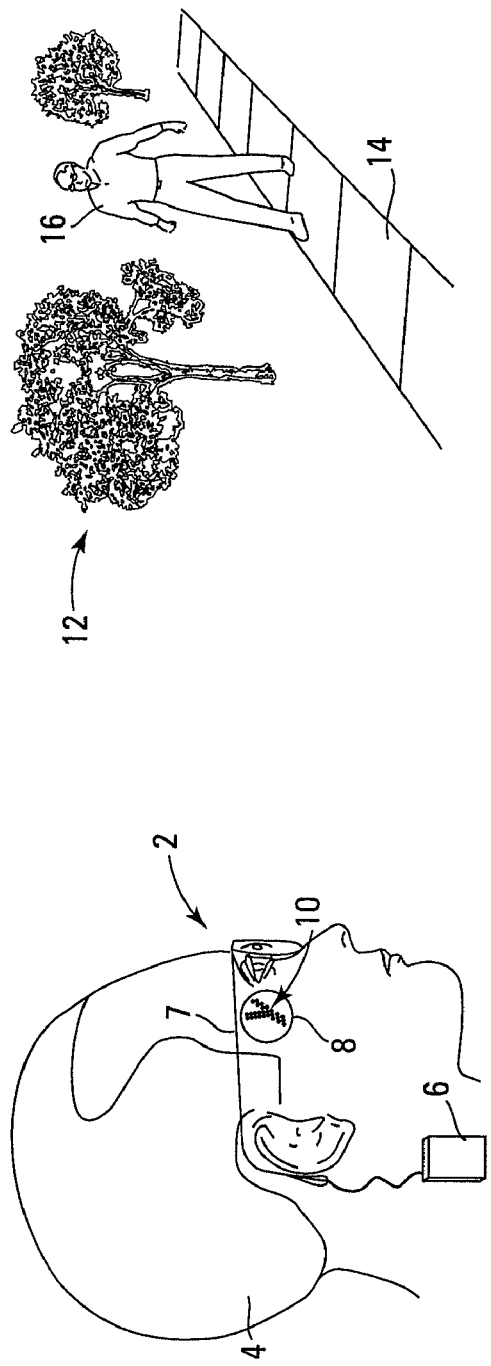
FIG. 1 is a perspective view of a sensing device including a visual prosthesis such as a retinal implant, according to an embodiment of the invention.

Newly available infrared sensing, such as infrared microbolometer array technology, is used for thermal imaging by sensing far infrared radiation, according to certain embodiments of the invention. Methods and apparatus for sensory substitution, sensory augmentation, vision prosthesis, or low-vision enhancement according to embodiments of the invention utilize thermal imaging to detect the temperature profile of objects and surroundings.

From an operational standpoint, seeing the world in temperature instead of visible light causes important shapes to stand out from the background. For example, the shape of a person's or animal's warm body stands out from a typically cooler background—color of clothing makes no difference. Since the temperature of an object is inherently more uniform than all of the possible colors of light, it is easier to translate the thermal image onto a tactile interface that can be touched. With such a system, the size, shape, and activities of people can be determined. At a high resolution, facial features, such as glasses and hair, can be identified. Paved sidewalks typically differ in temperature from dirt and grass. Exterior doors and windows are a different temperature than interior doors and walls. Building material made from metal or brick will retain heat differently than objects made from wood, plastic and glass. The heat of a vehicle's engine, tires, and exhaust stand out at a higher temperature than the surroundings. These thermal differences are used to create a thermal image of easily distinguishable temperature shapes, according to embodiments of the invention.

Thermal imaging is an excellent utilization of the limited resolution/bandwidth available to individuals with severe vision loss or through a retinal implant. Infrared provides an excellent way to discern and understand people-oriented scenes and outdoor scenes having heat-generating objects (e.g., traffic). A visible-spectrum sensor provides excellent assistance in performing many daily tasks, such as reading printed material. A fused combination of visible-spectrum and thermal imaging provides a benefit for understanding scenes that fall somewhere between these two extremes.

A two-dimensional system according to embodiments of the invention is useable in many ways. A tactile array is useable in a wearable form. Wearing a thermal imager and an array serves as a mobility aid. It is useable in public places, e.g. at live stage performances and public meetings. The system also is useable remotely. The thermal image of a television show, for example, is simultaneously sent over a cable system or phone line. The normal television broadcast provides the audio while a two-dimensional array of pins provides a thermal image of what is happening.

Public buildings include large, slightly heated displays and signs, hidden under the wallpaper of walls, for example, according to embodiments of the invention. These thermal aspects are invisible to a sighted person, but would stand out as a large sign to a person able to "see" or discern temperature differences. Such displays and signs optionally are active displays that change to provide general information and directions.

A simpler alternative to a two-dimensional array is a one-dimensional hand-held device that senses only in a narrow line extending from top to bottom. By holding it in the hand, the user visualizes a whole scene by sweeping the device from left to right, for example. The line of temperature controls a matching line of moving pins or other tactile interface. With practice, a person can recreate the shape of an object in their mind, with repeated scans in a manner roughly akin to feeling across an object with a hand, and sensing only a small portion at a time, but after several passes building a full mental model. According to additional embodiments of the invention, a user holds a thermal imaging tactile device in the hand or a soldier wears it on the head and sweeps it across a scene several times to form a mental image of the thermal shapes of the surrounding objects.

FIG. 1 illustrates interface 2 according to an embodiment of the invention, for communicating sensed thermal images to user 4. Processor 6 receives thermal image data from a detector, e.g. a detector supported by eyeglasses 7, as will be described. Processor 6 transmits corresponding signals to a retinal implant or other visual prosthesis, illustrated schematically at 8, that is in or in communication with the wearer's eye. Processor 6 processes thermal image data in real-time. Retinal implant or visual prosthesis 8 includes electrodes that stimulate the nerves in the retina directly, according to one example. More specifically, implant or visual prosthesis 8 creates pattern 10, which is perceived by user 4 as an image corresponding to the user's external environment as sensed by the detector.

Figure 2:
FIG. 2 shows a scene external to a thermal imager, according to an embodiment of the invention.

FIG. 2 illustrates one such external environment: scene 12, which corresponds to pattern 10. Scene 12 includes sidewalk 14 and person 16. As person 16 moves along sidewalk 14 or as scene 12 otherwise changes, pattern 10 of implant or visual prosthesis 8 changes accordingly. Pattern 10 as communicated by implant or visual prosthesis 8 to user 4 thus is not "all or nothing"; instead, implant or visual prosthesis 8 simultaneously conveys to user 4 different information corresponding to portions of external scene 12 having different thermal characteristics, e.g. sidewalk 14 and person 16.

Scene 12 of FIG. 2 is an outdoor scene, including soil and trees or bushes along with sidewalk 14 and person 16. If scene 12 were viewed only with a visible-light imaging device, e.g. as an aid to a blind or visually impaired person, complex processing of the image in real time would be required to identity the difference between person 16 and the bushes, and sidewalk 14 and the soil, for example. A thermal image, however, more easily distinguishes person 16 from the vegetation and the concrete of sidewalk 14 from the soil, because of the temperature difference between these types of objects.

The resolution possible with thermal imaging is less than that of a normal human eye, but thermal imaging provides an advantage over visible-spectrum imaging for resolution-limited and processing-limited applications. The thermal image is invariant to objects and background having similar color and variations in lighting conditions, for example. As a result, far less resolution and processing power are required to identify contrast between different objects or between objects and background, when the scene includes differing temperatures. The same is true for other scenes that have heat-generating objects beyond those specifically shown in FIG. 2, for example cars, busses, light bulbs etc. Moreover, a visible image generally requires complex edge-detection processing to differentiate objects in a scene. In the thermal image corresponding to scene 12, on the other hand, the concrete of sidewalk 14 simply is a different temperature than the soil, for example, and person 16 walking has a different temperature than other surrounding objects. The processing complexity and other complexities involved in distinguishing between the different portions of scene 12 thus are reduced.

Figure 3:
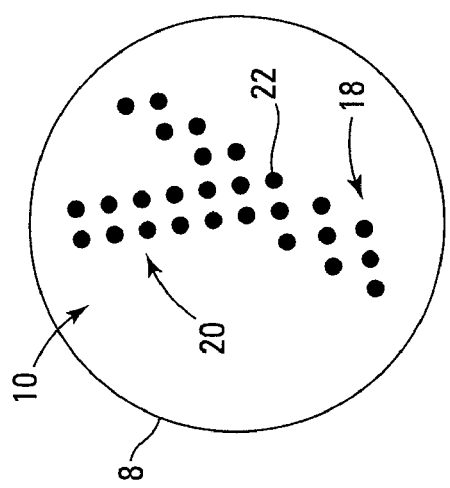
FIG. 3 shows a representation of the FIG. 2 scene, according to an embodiment of the invention.

FIG. 3 shows a close-up view of pattern 10 created by retinal implant or visual prosthesis 8. Portion 18 of pattern 10 corresponds to sidewalk 14 of FIG. 2, and portion 20 of pattern 10 corresponds to person 16 of FIG. 2. Each dot 22 of pattern 10 optionally corresponds to one or more sensing elements of a detector used to sense scene 12.

Figure 4:
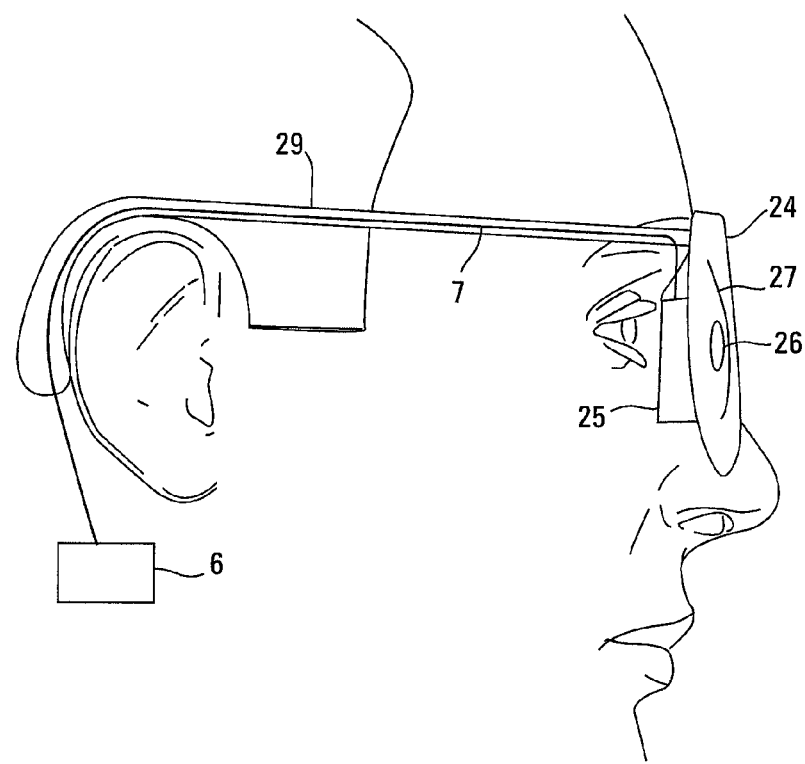
FIG. 4 shows a thermal imaging array behind eyeglasses including one or more germanium lenses, according to an embodiment of the invention.

FIG. 4 shows eyeglasses 7 that are used to support such a detector, in this case thermal imager 25. Thermal imagers that are based on uncooled microbolometer arrays, for example, are small enough to fit behind the lens of glasses 7. Other imagers are also contemplated. One possible lens material for use with glasses 7 is germanium, which is opaque to visible light and thus appears black when viewed in the visible spectrum. Germanium lens 26 is mounted within darkened glass 27 of glasses 7. The resulting effect is to make imager 25 virtually or completely unnoticeable. Electrical connectors to and from a thermal image array of imager 25, as will be described, are hidden by and/or directed along one or both arms 29 of glasses 7. Such lines travel to another point on the body of the wearer, where image data is processed, for example. According to one embodiment, processor 6 processes data and send signals to retinal implant or visual prosthesis 8, as previously described.

Figure 5:
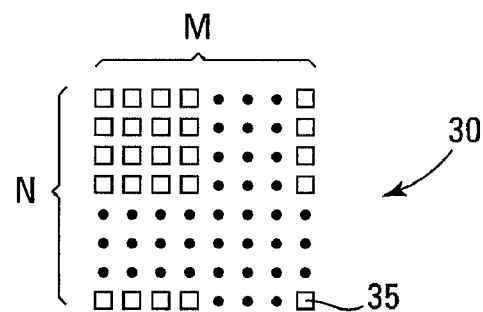
FIG. 5 shows a two-dimensional N×M elemental organization of an array of infrared radiation detecting elements, according to an embodiment of the invention.

FIG. 5 shows a detector suitable for use according to embodiments of the invention, in the form of thermal imaging array 30. Thermal imaging array 30 includes individual sensing elements 35 disposed in an N×M array. Each sensing element 35 is or corresponds to a pixel, for example, and corresponds to one or more of the dots of pattern 10. Array 30 may be of various grid densities, e.g. to provide varying spatial resolution of the temperature distribution of an observed scene or environment. Further, a one-dimensional array, or an array of other dimensions, or an array of different shapes, e.g. circular, polygonal, or other regular or irregular shape, also are contemplated according to embodiments of the invention.

Thermal sensor arrays according to embodiments of the invention are especially adapted to detect thermal radiation in a wavelength range of about 8 to about 14 µm, i.e. the far-infrared range. Of course, other wavelength detection ranges are also contemplated, e.g. mid-infrared (about 2 to about 5 µm) and near-infrared (about 0.75 to about 1.2 µm). Such arrays optionally are in the form of microbolometer imaging arrays.

Figure 6:
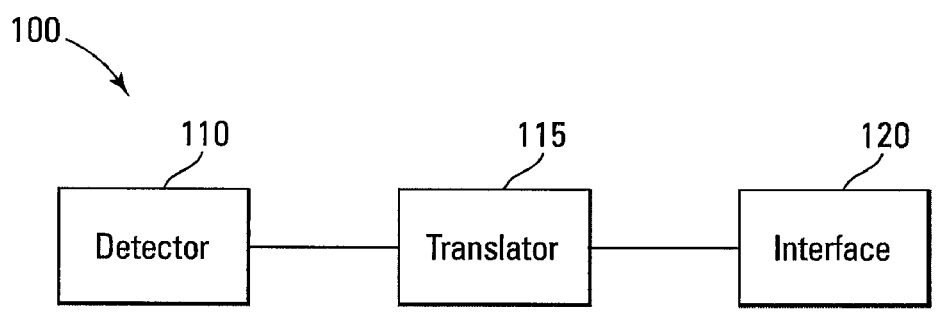
FIG. 6 is a schematic illustration of a detector, translator, and interface, according to an embodiment of the invention.

Turning to FIG. 6, apparatus 100 for obtaining thermal data comprises thermal detector 110, e.g. in the manner of array 30, adapted to sense thermal characteristics of an environment, such as scene 12. Detector 110 uses a plurality of pixels or sensing elements, e.g. in the manner of sensing elements 35 of FIG. 5. Pixel translator 115 is operably coupled with detector 110 and is adapted to translate pixel data of thermal detector 110 to a lower resolution. Interface 120, e.g. retinal implant or visual prosthesis 8, or a tactile or haptic interface, to be described, is operably coupled with pixel translator 115. Interface 120 is adapted to visually or non-visually communicate the thermal characteristics of the environment to a user of apparatus 100, optionally at a lower resolution than sensed by thermal detector 110.

Figure 7:
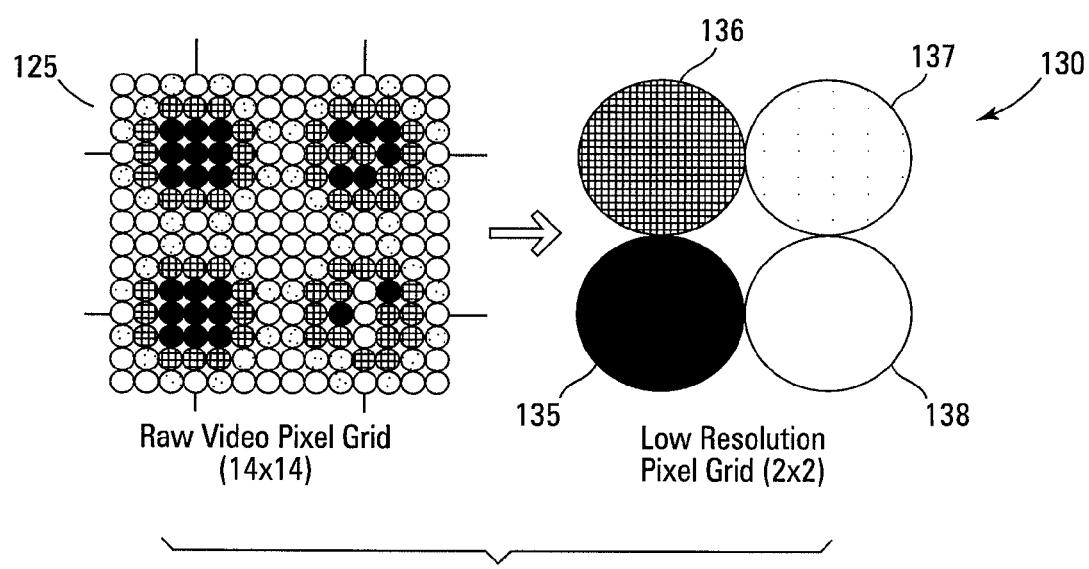
FIG. 7 is a diagram showing pixel resolution translation such that resolution of a thermal array is reduced to correspond to a tactile or haptic interface, according to an embodiment of the invention.

FIG. 7 shows high-resolution pixel data at e.g. 125. According to the illustrated embodiment, high-resolution pixel data 125 is, or corresponds to, raw video pixel data in a 14×14 grid, received from thermal detector 110. Translator 115 converts 14×14 high-resolution grid 125 according to this example into low-resolution pixel data or grid 130, which is a 2×2 grid. Of course, other grid dimensions are contemplated for grids 125 and 130. Each sensing element 35 of array 30, and/or each dot 22 of pattern 10, for example, optionally corresponds to a single pixel 135-138 of low-resolution pixel data 130. According to the illustrated example, pixel 135 is "darkest" or has the strongest value, followed in order by pixels 136, 137, and 138. According to embodiments of the invention, dots 22 of pattern 10 are of variable intensity in implant or visual prosthesis 8, with a dot 22 corresponding to darkest pixel 135 having the greatest intensity or darkness, for example. A dot 22 corresponding to pixel 136 has a slightly lower intensity, followed by dots 22 corresponding to pixels 137 and 138.

Figure 8:
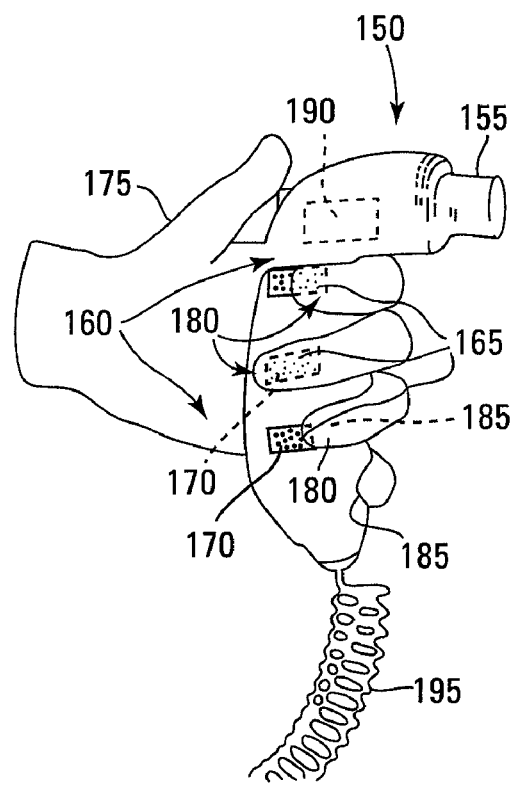
FIG. 8 is a perspective view of a handheld thermal imager, according to an embodiment of the invention.

FIG. 8 shows thermal imager 150 according to an embodiment of the invention. Thermal imager 150 includes imaging device 155, which includes thermal imaging array 30 shown in FIG. 5, for example. Imaging device 155 is, or includes, a microbolometer imaging device, according to one example. Imaging device 155 senses thermal characteristics of a scene external to imager 150, for example scene 12 of FIG. 2. Imager 150 also includes tactile interface 160, which is operably coupled with imaging device 155 and is adapted to receive input that is based on the scene sensed by the thermal imaging array and to convey tactile information based on the scene to a user of thermal imager 150. Tactile interface 160 is adapted to simultaneously convey to the user different tactile information corresponding to portions of external scene 12 having different thermal characteristics.

Tactile interface 160 includes one or more tactile arrays 165, for example three electromechanical pin arrays 165, each including a plurality of pins 170. Each pin array 165 generally corresponds to all or a portion of a thermal imaging array of imaging device 155. According to one example, the number of pins in one or more of pin arrays 165 is directly related to the number of pixels or other imaging elements of the thermal imaging array. Each pin 170 is of adjustable height, and imager 150 optionally is adapted to change the height of pins 170 based on the thermal characteristics sensed by the pixels of the thermal imaging array. According to the previously described example, pins 170 of tactile interface 160 are raised or otherwise actuated to form a pattern generally corresponding to sidewalk 14 and person 16 of scene 12. Other pins of interface 160 are not raised, according to the features of scene 12. The entire interface 160 may be of any desired shape, size, or density. Each pin array 165 of interface 160 optionally corresponds to a single thermal sensing array 30, according to one embodiment, but embodiments of the invention also contemplate correlating a portion of a single sensing array 30 to each pin array 165 such that the image sensed by array 30 is distributed across the entire interface 160. Embodiments of the invention also contemplate correlating sensing array 30 in its entirety to each pin array 165, such that the image sensed by array 30 is repeated multiple times across interface 160.

Each pin 170 or other tactile element is adapted to have its projected height changed, based on the value of its corresponding low-resolution pixel. According to one pixel height-variation strategy, a pin 170 corresponding to darkest pixel 135 (FIG. 7) has the greatest projected height and thus creates the strongest tactile sensation for a user of imager 100. A pin 170 corresponding to pixel 136 has a slightly lower projected height, followed by pins 170 corresponding to pixels 137 and 138. Those of ordinary skill in the art will appreciate the wide variety of ways to associate projected pin height with the corresponding value of pixels in grid 130. Interface 120 is a haptic interface adapted to communicate the thermal characteristics of the sensed environment to the user, using the user's sense of touch.

Thermal imager 150 is sized and/or shaped to be readily held in hand 175 of a human user; e.g. imager 150 is a handheld unit. Tactile interface 160 comprises three tactile arrays 165 spaced apart on the handheld unit. Of course, any number of arrays 165, e.g. one, two, three, four, five or more, are contemplated according to embodiments of the invention. Tactile arrays 165 of FIG. 8 are fingertip tactile arrays adapted to contact fingertips 180 of hand 175. Imager 150 of FIG. 8 also includes fingergrips 185, e.g. ridges or depressions, generally aligned with fingertip tactile arrays 165 of tactile interface 160. Of course, other placement of tactile array(s) 165 is contemplated, for example to contact the palm or other portion of hand 175, or another portion of the user's body. The handheld nature of imager 150 according to e.g. the FIG. 8 embodiment allows a user to point imager 150 in any desired direction. Tactile interface 160 indicates the scene or environment sensed by imaging device 155 in real time, as imager 150 is pointed at e.g. different objects, persons, and the like. As a user moves imager 150 up and down or side-to-side in real time, the user can gain a mental picture of their environment based on tactile interface 160.

Imager 150 further comprises processor 190 for receiving output from imaging device 155 and for generating input to tactile interface 160. As illustrated, processor 190 optionally is disposed within the handheld unit. Alternatively, or additionally, imaging device 155 and tactile interface 160 are adapted to communicate with a processor external to imager 150, via cord or cable 195 or other link. Imager 150 also is adaptable to communicate with retinal implant or visual prosthesis 8 or any of the user interface devices described or referenced herein.

Figure 9:
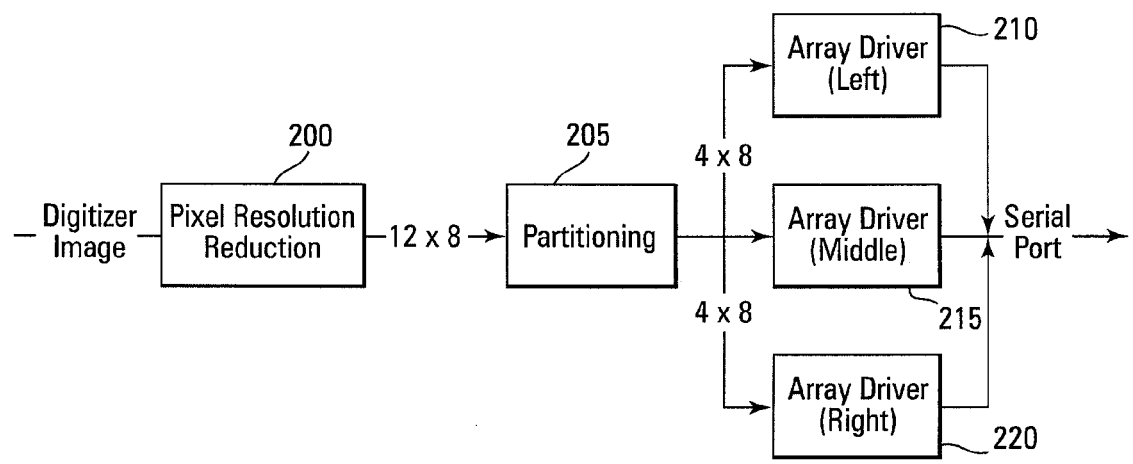
FIG. 9 is a schematic illustration of software elements for driving one or more tactile arrays, according to an embodiment of the invention.

FIG. 9 illustrates software elements for driving one or more tactile arrays of tactile interface 160. According to one embodiment, the software partitions a reduced-resolution 12×8 image into three sets of 4×8 pixels. An array driver activates each tactile array, e.g. each tactile array 165 of handheld imager 150 in FIG. 8, according to the intensity level of the reduced-resolution pixel grid illustrated in FIG. 7, for example. Serial data port commands or other commands control the movement of pins 170 in the tactile arrays. A pixel map to a serial command driver drives three tactile arrays, one for the left finger, one for the middle finger, and one for the right finger of a human user, for example. More specifically, in FIG. 9, pixel resolution reduction block 200 receives input from imaging device 155 or other digitizer, and outputs a 12×8 reduced-resolution image. Partitioning block 205 divides the 12×8 image into three 4×8 pixel maps, which are sent to array drivers 210, 215, 220 for the left, middle, and right fingertip arrays respectively.

Figure 10:
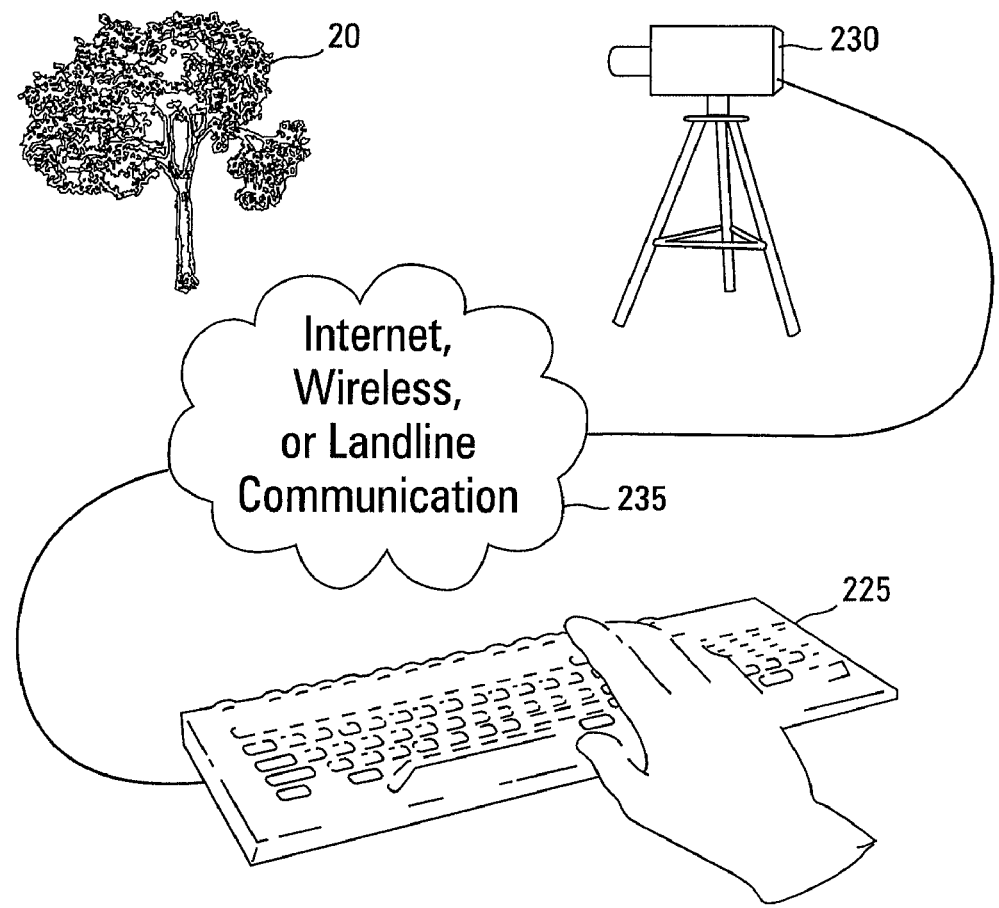
FIG. 10 is a diagram showing a thermal imaging array sending data through the Internet or other link to a person having an electromechanical array or other interface, according to an embodiment of the invention.

FIG. 10 shows how a thermal image of scene 12 is sent electronically to a remote location, e.g. a personal computer including keyboard 225, for controlling a remote haptic interface or other device at a distance from thermal camera or other imager 230. Alternatively, the thermal image is sent electronically directly to the haptic interface, in the manner described previously. Scene 12 is observed by thermal camera 230. The data from thermal camera 230 is sent, either in real-time or in a time-delayed format, over electronic media or communication feature 235. Media or communication feature 235 optionally includes the Internet, phone lines, wireless or cellular communication or communication networks, transferable storage media such as CD-ROM, discs, and the like, or other modes. An interface, such as previously described retinal implant or visual prosthesis 8 or interface 160, and/or a device under control of a personal computer or other controller, interfaces to a user a representation of the thermal image generated by camera 230. Remote sensing and/or analysis thus is provided, according to embodiments of the invention.

Figure 11:
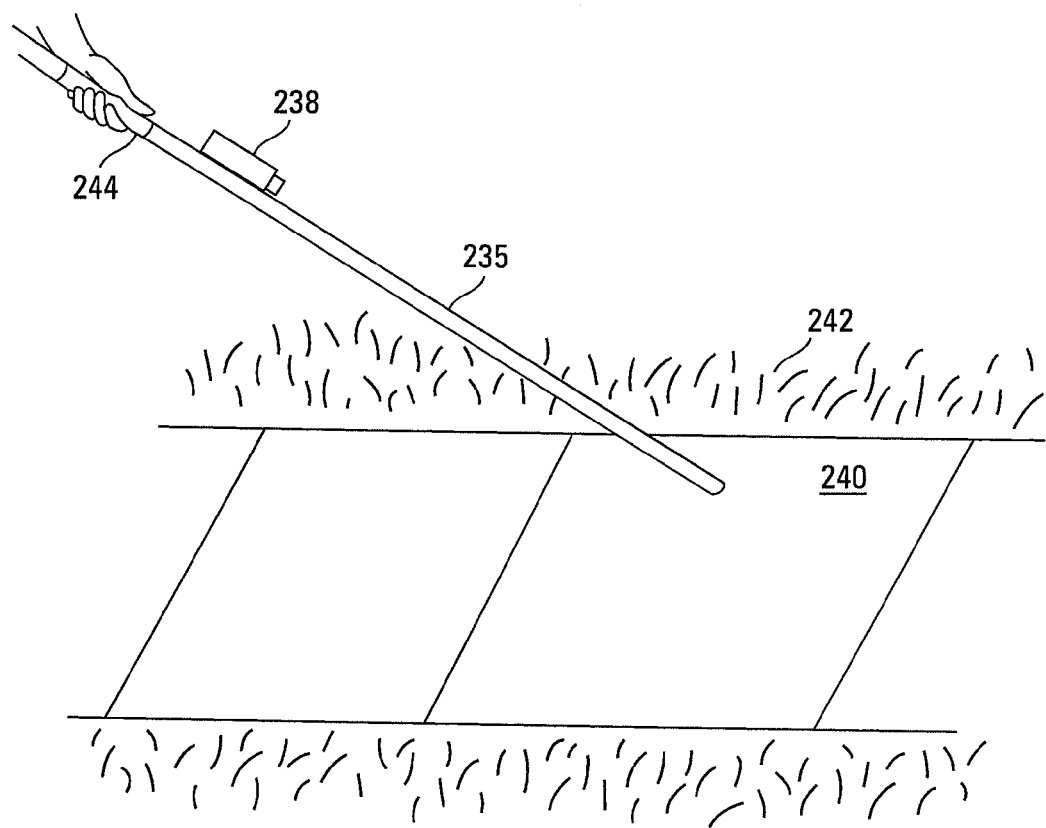
FIG. 11 shows a thermal imager supported on a cane, according to an embodiment of the invention.

FIG. 11 shows a thermal imager according to an embodiment of the invention used with cane 235, e.g. a cane for assisting blind or visually impaired persons. Imager 238 is supported on cane 235 as shown, and preferably is a small, low-cost thermal imager. The imager optionally is set to focus on the area at the tip of cane 235. This configuration senses a change in the material at which cane 235 is pointed. Pavement 240, for example, has a different temperature than soil or grass 242. Other examples include transitions between different materials and between different areas, e.g. transitions between wood, tile or carpet. In an outdoor setting, especially, different materials and areas retain thermal energy differently. The thermal image detected by imager 238 is interfaced to a user of cane 235 with an interface, e.g. retinal implant or visual prosthesis 8, or a haptic interface, such as tactile interface 160, at a handle area 244 of cane 235 or other desired location.

Figure 12:
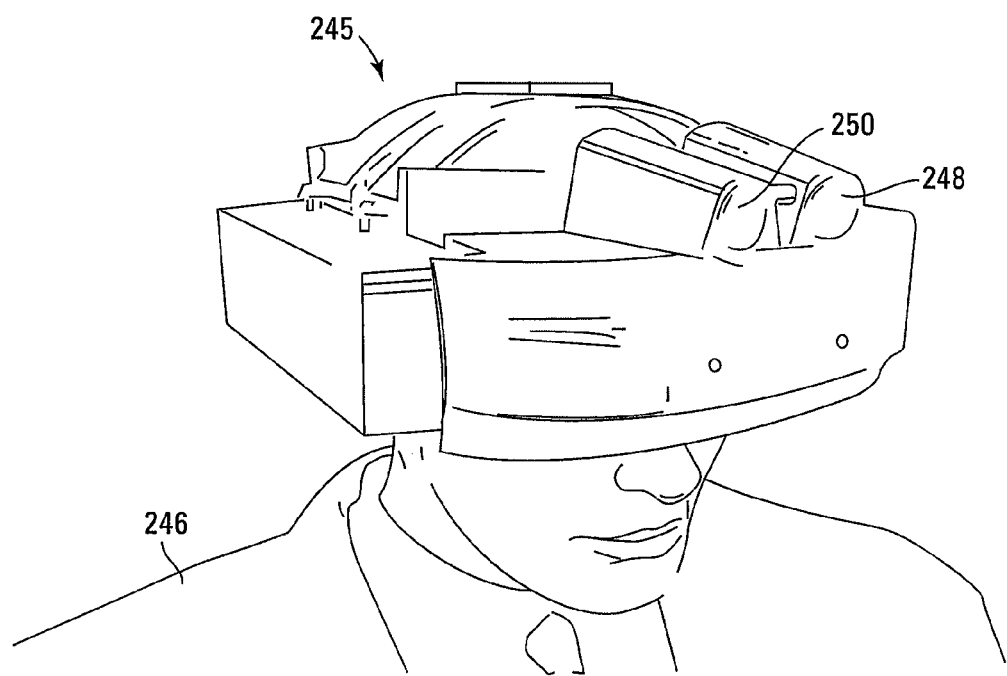
FIG. 12 shows a thermal imager at least partially supported on a head-mounted, low-vision enhancement device, according to an embodiment of the invention.

FIG. 12 shows low-vision enhancement system 245, mounted on the head of user 246. A low-vision enhancement system according to this embodiment presents a visible image, that has been processed in real-time, to a head-mounted display of the system. Processing optionally modifies the image in a manner that enhances the visible image for the unique vision problem of wearer 246. Visible camera 248 is mounted on system 245 to allow user 246 to aim camera 248 with head movement. System 245 additionally includes thermal imaging device 250, e.g. an imaging device in the manner previously described. One or more processing devices associated with visible camera 248 and thermal imaging device 250 optionally fuse the thermal and visual images that are generated, and/or select one type of image over another. Additional details regarding simultaneous visible and thermal imaging are described with respect to FIGS. 17-18 below.

Figure 13:
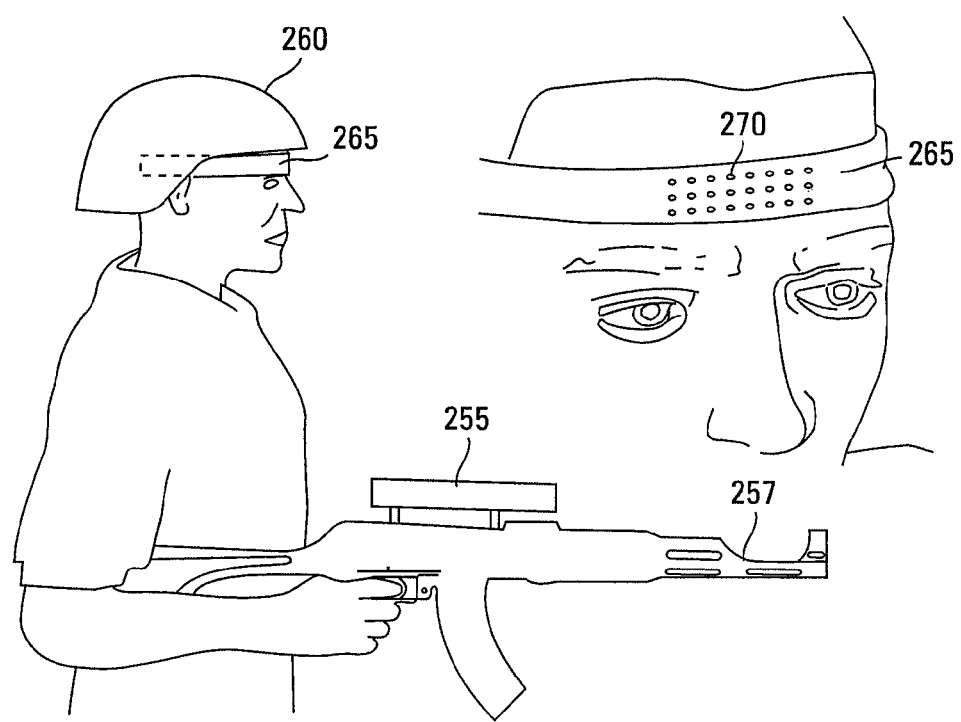
FIG. 13 shows a thermal imager at least partially mounted on one of a weapon and a headband or helmet, according to an embodiment of the invention.

According to the FIG. 13 embodiment, a non-visual thermal interface is used by a person, e.g. a soldier, having normal vision. Thermal imager 255 is mounted on weapon 257 or other device that is aimed. In a dark or smoke-filled area, for example, normal vision likely is reduced. The user may not want to have peripheral vision hampered by vision aids such as night goggles, for example, and embodiments of the invention thus are especially applicable in those situations. The user's helmet 260 includes headband 265, which supports an array of electromechanical vibrators 270, for example. Pins 170 or other electrotactile elements optionally are used instead of or in addition to vibrators 270, and headband 265 also is useable independently of helmet 260. Electromechanical vibrators 270 or other devices stimulate skin on the wearer's head as thermal imager 255 is scanned or moved to survey an environment or scene. A human being, for example, that would be difficult to see with normal vision because of low lighting or smoke, is readily identified with thermal imaging through the haptic interface in the form of vibrators 270. When sensed body temperature is felt by the user via the haptic interface, the intensity of vibration and its location within the haptic array conveys to the user that imager 255 is pointing e.g. directly at a human or other heat source. These embodiments also have application to firefighting, law enforcement, security, hunting, and other uses.

Figure 14:
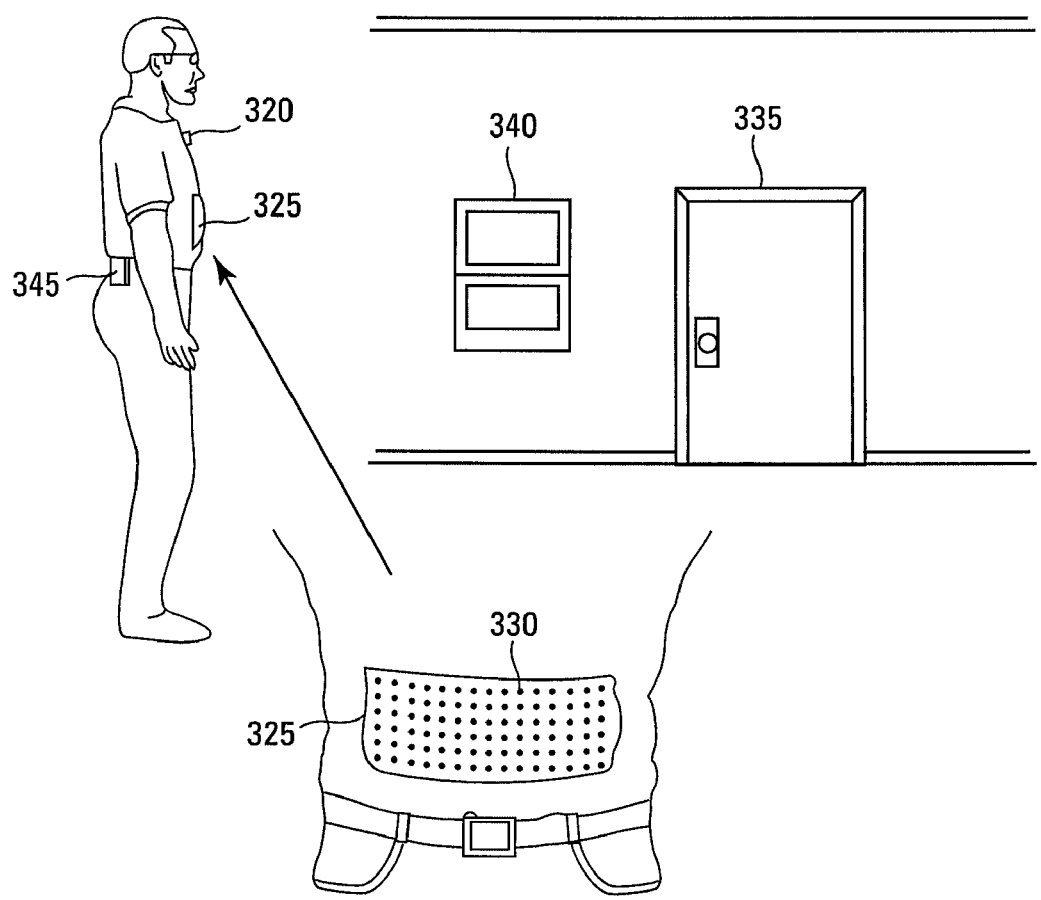
FIG. 14 shows a worn thermal image array feeding temperature data from a scene to an electro-tactile array on the abdomen.

In FIG. 14, a user is wearing imager 320, comprising a thermal imaging array, on their chest or upper body area. Data from the thermal imaging array is interfaced to the person with electrotactile array 325. Electrotactile array 325 includes an array of electrodes 330 that stimulate the skin in proportion to corresponding information sensed from a scene like scene 12 in FIG. 2. Array 325 is illustrated as being located on the abdomen of the user, but other body positions are contemplated according to embodiments of the invention, including the back, head, forehead, hand, or tongue, for example. In FIG. 14, array 325 is presenting to a user an image of external door 335 and window 340. The temperature of external doors and windows such as 335, 340 is often different than the interior room temperature, presenting a clear image to the user. The image is processed by a body-worn processor 345, for example. Processor 345 drives electrotactile array 325 to create a representation of the image as shown.

Figure 15:
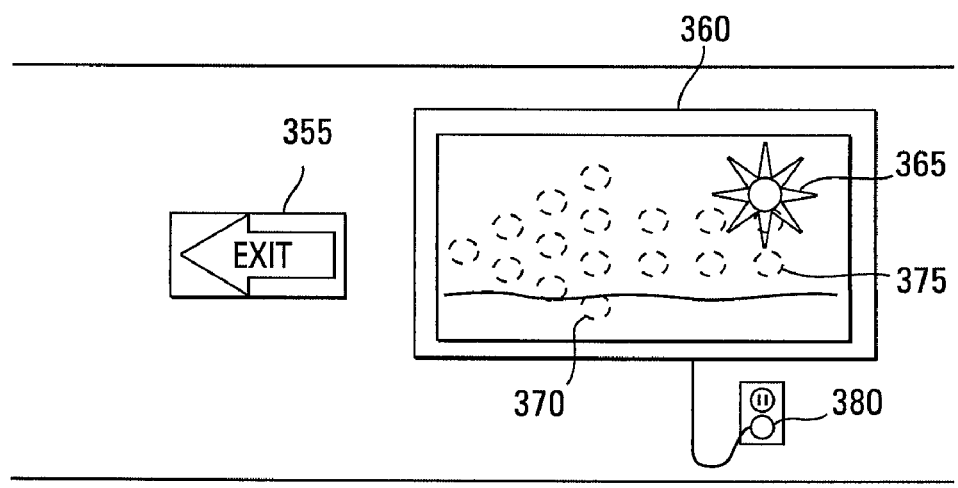
FIG. 15 shows thermal signs providing information, according to an embodiment of the invention.

FIG. 15 shows signs 355, 360 located so as to be interpreted by a person using a thermal imager as described herein. Sign 355 intended for normal vision is placed next to sign 360 intended for thermal vision. Sign 360 intended for thermal vision can appear to a person having normal human vision as a picture 365, while an entirely different thermal image 370, provided e.g. by heat sources 375, appears to a user of the thermal imager. Heat sources 375 are optionally powered by simple electrical power, e.g. at 380, and optionally are small heaters or even light bulbs, for example.

Figure 16:
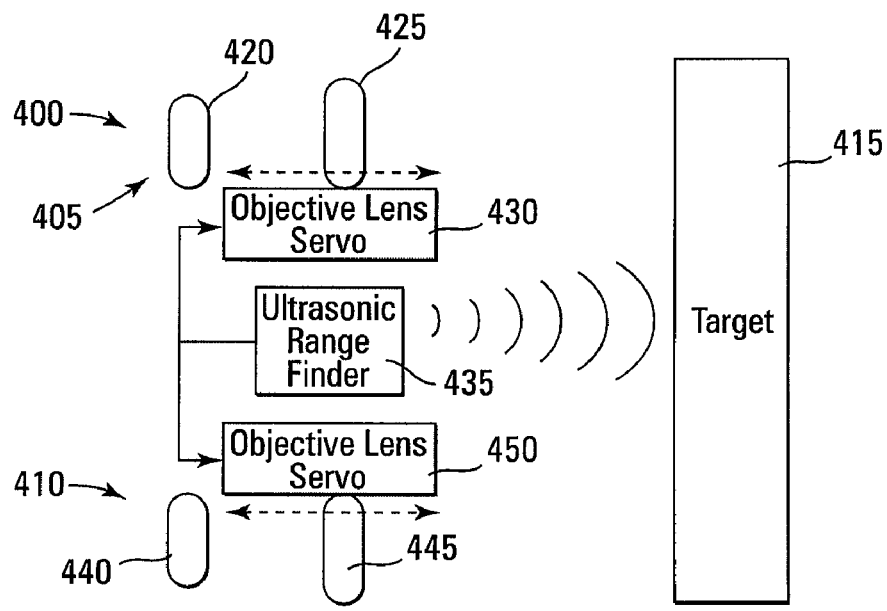
FIG. 16 is a schematic diagram showing a combined visual and infrared lens system, according to an embodiment of the invention.

FIG. 16 shows lens system 400, according to an embodiment of the invention, including visual lens system 405 and infrared or thermal lens system 410 for viewing target 415. Visual lens system 405 includes visual lenses 420, 425, the latter of which is moved by objective lens servo 430 based on readings from range finder 435, which for example is an ultrasonic range finder. Infrared or thermal lens system 410 include lenses 440, 445, the latter of which is moved by objective lens servo 450 based on readings from range finder 435.

Figure 17:
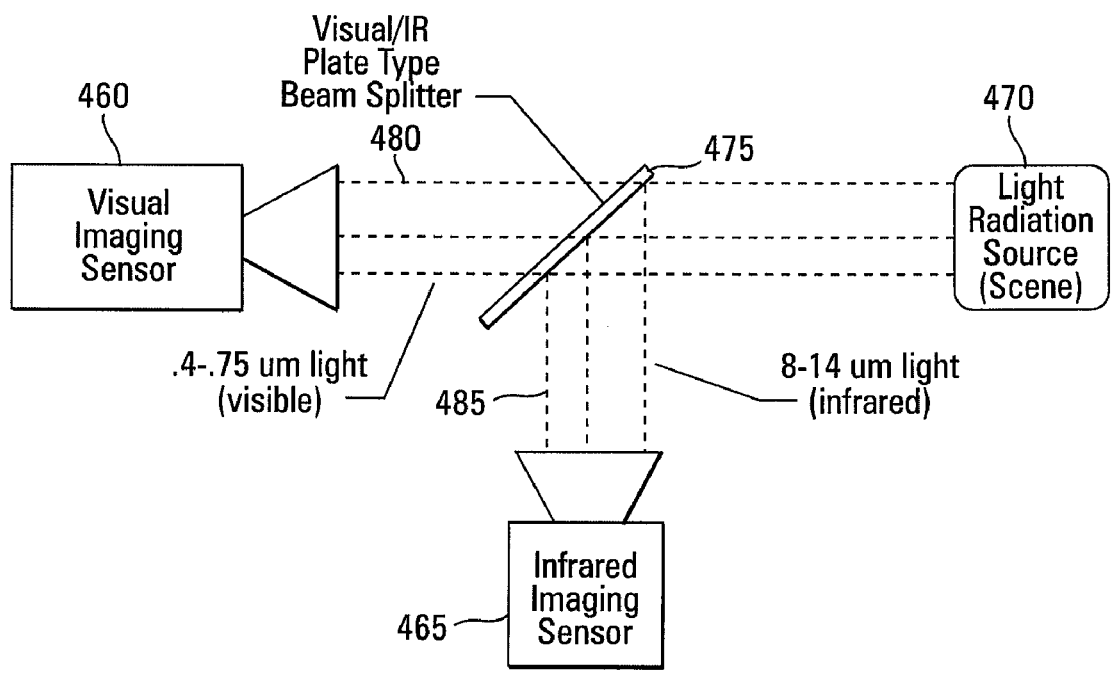
FIG. 17 is a schematic diagram showing combined visual and infrared imaging sensors, according to an embodiment of the invention.

FIG. 17 shows combined visual and infrared imaging sensors, according to an embodiment of the invention. Visual imaging sensor 460 and thermal or infrared imaging sensor 465 view light radiation source 470, which for example is a scene similar to scene 12 in FIG. 2. Visual/IR or visual/thermal plate-type beam splitter 475 splits radiation emanating from source 470 into visible portion 480, e.g. in the 0.4 to 0.75 µm range, and thermal or infrared portion 485, e.g. in the 8-14 µm range. The embodiments shown in FIGS. 16-17 are useable with any of the previously described embodiments, for example low-vision enhancement device 245 shown in FIG. 12, or eyeglasses 7 shown in FIG. 4.

Embodiments of the invention also extend to computer readable media containing software for operating any of the above-described devices. According to one example, at least one computer-readable medium has stored thereon a computer program that, when executed by a processor, causes operation of apparatus for obtaining thermal data, the apparatus including a thermal detector adapted to sense thermal characteristics of an environment using a plurality of pixels, the program comprising logic for translating pixel data generated by the thermal detection apparatus to a lower resolution, and logic for communicating the thermal characteristics of the environment to a user of the apparatus at a lower resolution than sensed by the thermal detector.

Thus, embodiments of the invention provide methods and apparatus for sensory substitution, vision prosthesis, or low-vision enhancement utilizing thermal sensing to detect the temperature of objects and surroundings. Although specific embodiments have been illustrated and described herein for purposes of description, it will be appreciated by those of ordinary skill in the art that a wide variety of alternate and/or equivalent implementations calculated to achieve similar purposes may be substituted for the specific embodiments shown and described, without departing from the scope of the present invention. For example, a wide variety of visual prostheses and/or tactile interfaces are contemplated, in a wide variety of locations on or in communication with the body. Correspondence between the pins, tactile elements or other elements of the interfaces, and the pixels of the low-resolution pixel grids described herein, optionally is 1:1 or any other desired ratio. Similarly, the correspondence between the pixels of the high-resolution and low-resolution grids described herein is selectable to be any desired ratio, as is the correspondence between the pixels or sensing elements of the thermal imaging arrays and the pixels of the high-resolution grids or low-resolution grids, or the pins or tactile elements of the tactile arrays. Any of the detectors or imagers described herein optionally are used with any of the interfaces, e.g. implant or other visual prosthesis 8, tactile interface 160, etc. Those with skill in the chemical, mechanical, electromechanical, electrical, or computer arts will readily appreciate that the present invention may be implemented in a very wide variety of embodiments. This application is intended to cover any adaptations or variations of the embodiments discussed herein.

What is claimed is:

1. A sensory substitution device, comprising:
   an imaging device comprising a thermal imaging array for sensing thermal characteristics of a scene external to the sensory substitution device, wherein the thermal imaging array is a passive far infrared imaging array; and
   a visual prosthesis, operably coupled with the imaging device, adapted to continuously receive input based on the scene sensed by the thermal imaging array and to convey information based on the scene to a user of the sensory substitution device, wherein the visual prosthesis is adapted for use by blind or low-vision persons and where the visual prosthesis is also adapted to continuously and simultaneously convey to the user different visual information corresponding to portions of the scene having different thermal characteristics;
   wherein the visual prosthesis is a low effective bandwidth information channel visual prosthesis and comprises one of a retinal implant, a tactile interface, and a haptic interface.

2. The device of claim 1, wherein the thermal imaging array comprises a microbolometer imaging array.

3. The device of claim 1, further comprising a pixel translator, operably coupled with the thermal imaging array, adapted to translate pixel data of the thermal imaging array to a lower resolution.

4. The device of claim 1, further comprising a processor for receiving output from the imaging device and for generating said input to the visual prosthesis.

5. A thermal imager, comprising:
   an imaging device comprising a thermal imaging array for sensing thermal characteristics of a scene external to the thermal imager utilizing passive far infrared sensing; and
   a tactile interface, operably coupled with the imaging device, adapted to continuously receive input based on the scene sensed by the thermal imaging array and to convey tactile information based on the scene to a user of the thermal imager, wherein the tactile interface is a low effective bandwidth information channel and is adapted to continuously and simultaneously convey to the user different tactile information corresponding to portions of the scene having different thermal characteristics;
   wherein the thermal imager is adapted for use by blind or low-vision users.

6. The imager of claim 5, wherein the tactile interface comprises an array of height-adjustable pins generally corresponding to the thermal imaging array; further wherein the imager is adapted to change the height of the pins based on the thermal characteristics of the external scene.

7. The imager of claim 5, wherein the thermal imager is a handheld unit.

8. The imager of claim 5, wherein the thermal imaging array comprises a microbolometer imaging array.

9. The imager of claim 8, wherein the microbolometer imaging array and the tactile interface are supported by a common housing.

10. Apparatus for obtaining thermal data, the apparatus comprising:
    a passive far infrared thermal detector adapted to continuously sense thermal characteristics of an environment using a plurality of pixels;
    a pixel translator, operably coupled with the thermal detector, adapted to translate the continuously sensed pixel data of the thermal detector to a lower resolution; and
    an interface, operably coupled with the pixel translator, adapted to continuously communicate the thermal characteristics of the environment from the pixel translator to a blind or visually impaired user of the apparatus at a lower resolution than sensed by the thermal detector;
    wherein the interface is a low effective bandwidth information channel; and
    wherein the interface is one of a retinal implant, a tactile interface, and a haptic interface.

11. The apparatus of claim 10, wherein the interface comprises a visual prosthesis.

12. The apparatus of claim 10, wherein the interface is a one or two dimensional haptic interface adapted to communicate the thermal characteristics of the environment to the user using the user's sense of touch.

13. The apparatus of claim 10, wherein the pixel translator translates high-resolution pixel data from the thermal detector to low-resolution pixel data for the interface; further wherein the interface comprises a plurality of tactile elements in a one or two dimensional array, each tactile element corresponding to a low-resolution pixel of the low-resolution pixel data.

14. The apparatus of claim 10, wherein the apparatus is at least partially supported on a cane; further wherein the tactile interface is supported at a handgrip of the cane and is adapted to contact the hand of a user of the cane.

15. The apparatus of claim 10, wherein the apparatus is adapted to present a fused combination of visible-spectrum and thermal characteristics to the user.

16. The apparatus of claim 10, wherein the apparatus is at least partially supported on a pair of eyeglasses.

17. The apparatus of claim 16, wherein the pair of eyeglasses comprises an eyeglass lens, further wherein the apparatus comprises a lens for thermal imaging mounted within the eyeglass lens.

18. The apparatus of claim 10, wherein the thermal detector comprises one or more thermal sensor arrays adapted to detect thermal radiation in a wavelength range of about 8 to about 14 μm.

19. Apparatus for obtaining thermal data, the apparatus comprising:
- a passive far infrared thermal detector adapted to sense thermal characteristics of an environment using a plurality of pixels;
- a pixel translator, operably coupled with the thermal detector, adapted to translate pixel data of the thermal detector to a lower resolution; and
- an interface, operably coupled with the pixel translator, adapted to communicate the thermal characteristics of the environment to a blind or visually impaired user of the apparatus at a lower resolution than sensed by the thermal detector;
- wherein the interface is a low effective bandwidth information channel;
- wherein the interface comprises a visual prosthesis; and
- wherein the visual prosthesis comprises a retinal implant.

20. At least one computer-readable medium having stored thereon a computer program that, when executed by a processor, causes operation of apparatus for use by blind or low-vision persons for obtaining thermal data, the apparatus including a passive far infrared thermal detector adapted to continuously sense thermal characteristics of an environment using a plurality of pixels, the program comprising:
- logic for continuously translating pixel data generated by the thermal detection apparatus to a lower resolution; and
- logic for continuously communicating the thermal characteristics of the environment to a blind or low-vision user of the apparatus at a lower resolution than sensed by the thermal detector;
- wherein the thermal characteristics of the environment are communicated to the blind or low-vision user through a low effective bandwidth information interface; and
- wherein the low effective bandwidth information interface is one of a retinal implant, a tactile interface, and a haptic interface.

* * * * *